US009186380B2

(12) United States Patent
Shi et al.

(10) Patent No.: US 9,186,380 B2
(45) Date of Patent: Nov. 17, 2015

(54) MINCED CARTILAGE SYSTEMS AND METHODS

(71) Applicant: AlloSource, Centennial, CO (US)

(72) Inventors: Yaling Shi, Larkspur, CO (US); Carolyn Barrett, Denver, CO (US)

(73) Assignee: AlloSource, Centennial, CO (US)

( * ) Notice: Subject to any disclaimer, the term of this patent is extended or adjusted under 35 U.S.C. 154(b) by 0 days.

(21) Appl. No.: 14/081,913

(22) Filed: Nov. 15, 2013

(65) Prior Publication Data

US 2014/0134212 A1    May 15, 2014

Related U.S. Application Data

(60) Provisional application No. 61/727,016, filed on Nov. 15, 2012.

(51) Int. Cl.
*A61K 35/32* (2015.01)

(52) U.S. Cl.
CPC ...................... *A61K 35/32* (2013.01)

(58) Field of Classification Search
CPC ..................................................... A61K 35/32
See application file for complete search history.

(56) References Cited

U.S. PATENT DOCUMENTS

| | | | |
|---|---|---|---|
| 4,932,973 A | 6/1990 | Gendler | |
| 5,582,752 A | 12/1996 | Zair | |
| 5,755,791 A | 5/1998 | Whitson et al. | |
| 5,968,096 A | 10/1999 | Whitson et al. | |
| 6,050,991 A | 4/2000 | Guillet | |
| 6,235,316 B1 | 5/2001 | Adkisson | |
| 6,607,524 B1 | 8/2003 | LaBudde et al. | |
| 6,638,271 B2 | 10/2003 | Munnerlyn et al. | |
| 6,645,764 B1 | 11/2003 | Adkisson | |
| 6,712,822 B2 | 3/2004 | Re et al. | |
| 6,872,226 B2 * | 3/2005 | Cali et al. ................ | 623/2.13 |
| 7,361,195 B2 | 4/2008 | Schwartz et al. | |
| 7,550,007 B2 | 6/2009 | Malinin | |
| 7,758,643 B2 | 7/2010 | Stone et al. | |
| 7,824,711 B2 | 11/2010 | Kizer et al. | |
| 7,838,040 B2 | 11/2010 | Malinin | |
| 7,875,296 B2 | 1/2011 | Binette et al. | |
| RE42,208 E | 3/2011 | Truncale et al. | |
| 8,012,206 B2 | 9/2011 | Schmieding | |
| 8,043,450 B2 | 10/2011 | Cali et al. | |
| 8,083,755 B2 | 12/2011 | Mathisen et al. | |
| RE43,258 E | 3/2012 | Truncale et al. | |
| 8,142,502 B2 | 3/2012 | Stone et al. | |
| 8,221,500 B2 | 7/2012 | Truncale et al. | |
| 8,318,212 B2 | 11/2012 | Malinin | |
| 8,497,121 B2 | 7/2013 | Yao et al. | |
| 8,585,753 B2 | 11/2013 | Scanlon et al. | |
| 8,641,775 B2 | 2/2014 | Harmon et al. | |
| 8,652,214 B2 | 2/2014 | Fritz et al. | |
| 8,652,507 B2 | 2/2014 | Kizer et al. | |
| 8,883,210 B1 | 11/2014 | Truncale et al. | |
| 8,945,535 B2 | 2/2015 | Steinwachs et al. | |
| 2004/0068256 A1 * | 4/2004 | Rizoiu et al. ................ | 606/13 |
| 2004/0078090 A1 | 4/2004 | Binette et al. | |
| 2004/0249464 A1 | 12/2004 | Bindseil | |
| 2005/0288796 A1 | 12/2005 | Awad et al. | |
| 2006/0210643 A1 | 9/2006 | Truncale et al. | |
| 2006/0241756 A1 | 10/2006 | Fritz et al. | |
| 2006/0275273 A1 | 12/2006 | Seyedin et al. | |
| 2007/0265705 A1 | 11/2007 | Gaissmaier et al. | |
| 2007/0299517 A1 * | 12/2007 | Davisson et al. .......... | 623/11.11 |
| 2008/0014179 A1 | 1/2008 | Ferree | |
| 2008/0160496 A1 | 7/2008 | Rzepakovsky et al. | |
| 2008/0269895 A1 | 10/2008 | Steinwachs et al. | |
| 2009/0010982 A1 | 1/2009 | Abrahams | |
| 2009/0024223 A1 | 1/2009 | Chen et al. | |
| 2010/0049322 A1 | 2/2010 | McKay | |
| 2010/0124776 A1 | 5/2010 | Shi | |
| 2010/0274362 A1 | 10/2010 | Yayon | |
| 2011/0045044 A1 | 2/2011 | Masinaei et al. | |
| 2011/0052705 A1 | 3/2011 | Malinin | |
| 2011/0091517 A1 | 4/2011 | Binette et al. | |
| 2011/0177134 A1 | 7/2011 | Harmon et al. | |
| 2011/0182961 A1 | 7/2011 | McKay | |
| 2011/0196355 A1 | 8/2011 | Mitchell et al. | |
| 2011/0262696 A1 | 10/2011 | Bayon | |
| 2011/0274729 A1 | 11/2011 | Collins | |
| 2012/0107384 A1 | 5/2012 | Yao | |
| 2012/0226354 A1 | 9/2012 | Alleyne | |
| 2012/0321878 A1 | 12/2012 | Landon et al. | |
| 2013/0030528 A1 | 1/2013 | Chen et al. | |
| 2013/0035676 A1 | 2/2013 | Mitchell et al. | |

(Continued)

FOREIGN PATENT DOCUMENTS

WO      2005/058207 A1     6/2005

OTHER PUBLICATIONS

Albrecht, F., et al. "Closure of Osteochondral Lesions Using Chondral Fragments and Fibrin Adhesive." Archives of Orthopaedic and Traumatic Surgery, vol. 101 (1983): pp. 213-217.
Allosource. (Sep. 2012). "DeNovo*NT: Natural Tissue Graft" [Brochure]. Centennial, CO. AlloSource. 2 pages.
Brittberg, M., M.D., et al., "Treatment of Deep Cartilage Defects in the Knee with Autologous Chondrocyte Translation." *The New England Journal of Medicine*. vol. 331, No. 14 (Oct. 6, 1994): pp. 889-895.
Farr, J., et al., "Chondral defect repair with particulated juvenile cartilage allograft." Electronic Poster. *International Cartilage Repair Society*, Sep. 26-29, 2010, Sitges/Barcelona, Spain. Retrieved from <http://posters.webges.com/icrs/epos> on Oct. 11, 2010, 14 pages.
Frisbie, D. D., et al. "In Vivo Evalutation of a One Step Autologous Cartilage Resurfacing Technique in a Long Term Equine Model." Poster #1355. *51st Annual Meeting of the Orthopaedic Research Society*, May 20-23, 2005. One page.

(Continued)

Primary Examiner — Ernst V Arnold
(74) Attorney, Agent, or Firm — Kilpatrick Townsend & Stockton LLP

(57) ABSTRACT

Compositions comprising a plurality of cartilage particles from a human adult cadaveric donor, wherein the cartilage particles comprise viable chondrocytes, and a biocompatible carrier are provided. Methods of manufacturing cartilage compositions comprising a plurality of cartilage particles from a human adult cadaveric donor are also provided.

18 Claims, 12 Drawing Sheets

(56) References Cited

U.S. PATENT DOCUMENTS

| | | |
|---|---|---|
| 2013/0122095 A1 | 5/2013 | Kestler et al. |
| 2013/0197654 A1 | 8/2013 | Samuelson et al. |
| 2013/0204392 A1 | 8/2013 | Law et al. |
| 2013/0344114 A1 | 12/2013 | Chang et al. |
| 2014/0012393 A1 | 1/2014 | Shin et al. |
| 2014/0017283 A1 | 1/2014 | Yoo et al. |
| 2014/0017292 A1 | 1/2014 | Yoo et al. |
| 2014/0024115 A1 | 1/2014 | Bogdansky et al. |
| 2014/0030309 A1 | 1/2014 | Yoo et al. |
| 2014/0058527 A1 | 2/2014 | Truncale et al. |
| 2014/0099709 A1 | 4/2014 | Presnell et al. |
| 2014/0134212 A1 | 5/2014 | Shi et al. |
| 2014/0212910 A1 | 7/2014 | Bhatia et al. |
| 2014/0222159 A1 | 8/2014 | Bursac et al. |
| 2014/0234272 A1 | 8/2014 | Vesey et al. |
| 2014/0255506 A1 | 9/2014 | Behnam et al. |
| 2014/0271454 A1 | 9/2014 | L'Heureux et al. |
| 2014/0271570 A1 | 9/2014 | Shi et al. |
| 2014/0287960 A1 | 9/2014 | Shepherd et al. |
| 2015/0004211 A1 | 1/2015 | Yoo et al. |
| 2015/0017222 A1 | 1/2015 | Yoo et al. |
| 2015/0140057 A1 | 5/2015 | Yoo et al. |

OTHER PUBLICATIONS

Knutsen, G., et al., "A Randomized Trial Comparing Autologous Chondrocyte Implantation with Microfracture: Findings at Five Years." *The Journal of Bone and Joint Surgery, Inc.* vol. 89-A, No. 10 (Oct. 2007): pp. 2105-2112.

Knutsen, G., et al., "Autologous Chondrocyte Implantation Compared with Microfracture in the Knee." *The Journal of Bone and Joint Surgery, Inc.* vol. 86-A, No. 3 (Mar. 2004): pp. 455-464.

Lu, Y., et al., "Minced Cartilage without Cell Culture Serves as an Effective Intraoperative Cell Source for Cartilage Repair." *Journal of Orthopaedic Research* (Jun. 2006): pp. 1261-1270.

Stone, K. R., et al. "Articular Cartilage Paste Grafting to Full-Thickness Articular Cartilage Knee Joint Lesions: A 2- to 12-Year Follow-up." *Arthroscopy: The Journal of Arthroscopc and Related Surgery*, vol. 22, No. 3 (Mar. 2006): pp. 291-299.

Strong, D.M., et al., "Freeze-Drying of Tissues." *Musculoskeletal Tissue Banking*. W. W. Tomford. New York. Raven Press, 1993. pp. 181-208 plus cover pages. Print.

Zimmer, "Articular Cartilage Repair: Basic Science." *Zimmer Technical Memo*. (2009) Zimmer, Inc. 3 pages.

Eyre, D. Collagen of articular cartilage, Arthritis Res. 4:30-35 (2002).

* cited by examiner

ADULT DONOR A (fluorescence readings)

JUVENILE DONOR B (fluorescence readings)

| | | Day 1 cell # 0.3cc | 6wk cell #.3cc explant | Cell outgrowth |
|---|---|---|---|---|
| Adult-124594 | Laser | 66490 | 956052 | 889562 |
| | Hand cut | 266033 | 987022 | 720989 |
| Juvenile-124953 | Laser | 772345 | 1012770 | 240425 |
| | Hand cut | 803742 | 1143297 | 339555 |

FIG. 4

(Donors C, D, E, F, and G)

| Donor # | Laser Cut | Hand cut | Denovo | | Laser Cut | Hand cut |
|---|---|---|---|---|---|---|
| 1 | 390,000 | 360,000 | 4176788 | | 85% | 91% |
| 2 | 1,433,333 | 176,666 | 813570.4 | | 88% | 71% |
| 3 | 295,000 | 237,500 | 1452609 | | 85% | 92% |
| 4 | 2,625,000 | 890,000 | | | 90% | 87% |
| 5 | 517,500 | 212,500 | | | 83% | 89% |
| | 1,052,167 | 375,333 | 2147656 | | 86% | 86% |
| | 989,536 | 295,846 | 1786092 | | 3% | 9% |

| | Laser Cut | Hand cut | Denovo | | Laser Cut | Hand cut |
|---|---|---|---|---|---|---|
| Trypan Blue | 1,052,167 | 375,333 | 2147656 | | 86% | 86% |
| Presto Blue | 2,607,441 | 2,672,802 | 1786092 | AVG | | |
| STDEV | 989,536 | 295,846 | | | 3% | 9% |
| | 1,108,534 | 1,397,028 | | STDEV | | |

FIG. 5

MINCED CARTILAGE SYSTEMS AND METHODS

CROSS-REFERENCES TO RELATED APPLICATIONS

This application claims benefit of priority of U.S. Provisional Application No. 61/727,016, filed Nov. 15, 2012, the entire content of which is incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Cartilage tissue can be found throughout the human anatomy. The cells within cartilage tissue are called chondrocytes. These cells generate proteins, such as collagen, proteoglycan, and elastin, that are involved in the formation and maintenance of the cartilage. Hyaline cartilage is present on certain bone surfaces, where it is commonly referred to as articular cartilage. Articular cartilage contains significant amounts of collagen (about two-thirds of the dry weight of articular cartilage), and cross-linking of the collagen imparts a high material strength and firmness to the tissue. These mechanical properties are important to the proper performance of the articular cartilage within the body.

Articular cartilage is not vascularized, and when damaged as a result of trauma or degenerative causes, this tissue has little or no capacity for in vivo self-repair. A variety of therapeutic solutions have been proposed for the treatment and repair of damaged or degenerated cartilage. Although such techniques may provide real benefits to patients in need thereof, still further advancements in the field of cartilage repair are desirable.

BRIEF SUMMARY OF THE INVENTION

In one aspect, cartilage compositions are provided. In some embodiments, the composition comprises: a plurality of cartilage particles from a human adult cadaveric donor age 15 years or older, wherein the cartilage particles comprise viable chondrocytes; and a biocompatible carrier.

In some embodiments, on average at least 50% of the chondrocytes in the cartilage particles are viable.

In some embodiments, the cartilage is articular cartilage. In some embodiments, the cartilage is non-decellularized cartilage. In some embodiments, the cartilage particles are from a human donor that is 18 years of age or older at the time of donation.

In some embodiments, the cartilage particles have an average thickness from about 0.25 mm to about 5 mm. In some embodiments, the cartilage particles have an average thickness from about 0.5 mm to about 2 mm. In some embodiments, the cartilage particles have an average length and/or an average width from about 0.1 mm to about 25 mm. In some embodiments, the cartilage particles have an average diameter from about 0.1 mm to about 25 mm. In some embodiments, the cartilage particles have an average volume of about 0.5 mm$^3$ to about 100 mm$^3$. In some embodiments, the cartilage particles have an average volume of about 0.5 mm$^3$ to about 30 mm$^3$.

In some embodiments, the biocompatible carrier comprises a cryopreservation medium. In some embodiments, the cryopreservation medium comprises dimethyl sulfoxide (DMSO) and serum.

In some embodiments, the composition further comprises a biological adhesive. In some embodiments, the biological adhesive is fibrin, fibrinogen, thrombin, fibrin glue, polysaccharide gel, cyanoacrylate glue, gelatin-resorcin-formalin adhesive, collagen gel, synthetic acrylate-based adhesive, cellulose-based adhesive, basement membrane matrix, laminin, elastin, proteoglycans, autologous glue, or a combination thereof.

In some embodiments, the composition further comprises demineralized bone. In some embodiments, the composition further comprises a bone or cartilage substrate seeded with stem cells.

In another aspect, methods of manufacturing a cartilage composition are provided. In some embodiments, the method comprises:
  obtaining cartilage tissue from a human adult cadaveric donor;
  mincing the cartilage tissue into a plurality of cartilage particles, wherein the cartilage particles comprise viable chondrocytes; and
  suspending the plurality of cartilage particles in a biocompatible medium.

In some embodiments, on average at least 50% of the chondrocytes in the cartilage particles are viable.

In some embodiments, the cartilage tissue is articular cartilage. In some embodiments, the cartilage tissue is non-decellularized cartilage. In some embodiments, the cartilage tissue is from a human donor that is 18 years of age or older at the time of donation.

In some embodiments, prior to the mincing step, the cartilage tissue is sliced to a thickness of about 0.25 mm to about 5 mm. In some embodiments, prior to the mincing step, the cartilage tissue is sliced to a thickness of about 0.25 mm to about 2 mm.

In some embodiments, the mincing step comprises cutting the cartilage tissue with a laser cutter, with a mechanical blade, or with a mechanical press. In some embodiments, the mincing step comprises cutting the cartilage tissue with a laser cutter. In some embodiments, the mincing step comprising cutting the cartilage tissue with the laser cutter at a speed from about 10% to about 50%, a power from about 0% to about 45%, and a frequency from about 10 Hz to about 2400 Hz.

In some embodiments, the cartilage tissue is minced into a plurality of cartilage particles having an average length and/or an average width from about 0.1 mm to about 25 mm. In some embodiments, the cartilage particles have an average diameter from about 0.1 mm to about 25 mm. In some embodiments, the cartilage tissue is minced into a plurality of cartilage particles having an average volume of about 0.5 mm$^3$ to about 100 mm$^3$. In some embodiments, the cartilage tissue is minced into a plurality of cartilage particles having an average volume of about 0.5 mm$^3$ to about 30 mm$^3$.

In some embodiments, following the mincing step, the plurality of cartilage particles are washed with a saline solution.

In some embodiments, the biocompatible carrier comprises a cryopreservation medium. In some embodiments, the cryopreservation medium comprises dimethyl sulfoxide (DMSO) and serum.

In some embodiments, prior to the suspending step, the method further comprises combining the plurality of cartilage particles with a biological adhesive. In some embodiments, the biological adhesive is fibrin, fibrinogen, thrombin, fibrin glue, polysaccharide gel, cyanoacrylate glue, gelatin-resorcin-formalin adhesive, collagen gel, synthetic acrylate-based adhesive, cellulose-based adhesive, basement membrane matrix, laminin, elastin, proteoglycans, autologous glue, or a combination thereof.

In some embodiments, prior to the suspending step, the method further comprises combining the plurality of cartilage particles with demineralized bone. In some embodiments, prior to the suspending step, the method further comprises combining the plurality of cartilage particles with a bone or cartilage substrate seeded with stem cells.

In another aspect, methods of repairing cartilage in a subject are provided. In some embodiments, the method comprises administering to the subject a composition as described herein (e.g., a composition comprising a plurality of cartilage particles from a human adult cadaveric donor age 15 years or older, wherein the cartilage particles comprise viable chondrocytes; and a biocompatible carrier).

In yet another aspect, methods of treating a defect in cartilage, bone, ligament, tendon, meniscus, joint, or muscle in a subject are provided. In some embodiments, the method comprises administering to the subject a composition as described herein (e.g., a composition comprising a plurality of cartilage particles from a human adult cadaveric donor age 15 years or older, wherein the cartilage particles comprise viable chondrocytes; and a biocompatible carrier).

In still another aspect, compositions for use in treating a defect in cartilage, bone, ligament, tendon, meniscus, joint, or muscle in a subject are provided. In some embodiments, the composition for use is a composition as described herein (e.g., a composition comprising a plurality of cartilage particles from a human adult cadaveric donor age 15 years or older, wherein the cartilage particles comprise viable chondrocytes; and a biocompatible carrier).

In still another aspect, kits comprising a composition as described herein (e.g., a composition comprising a plurality of cartilage particles from a human adult cadaveric donor age 15 years or older, wherein the cartilage particles comprise viable chondrocytes; and a biocompatible carrier) are provided. In some embodiments, the kits are used for treating a subject having a defect in cartilage, bone, ligament, tendon, meniscus, joint, or muscle. In some embodiments, the kits are used for treating a subject having a degenerative defect or injury cartilage, bone, ligament, tendon, meniscus, joint, or muscle; a subject having a traumatic defect or injury cartilage, bone, ligament, tendon, meniscus, joint, or muscle; or a subject having osteoarthritis.

BRIEF DESCRIPTION OF THE DRAWINGS

FIG. 4. Mean fluorescence readings for chondrocyte samples from an adult donor and from a juvenile donor, measured at day 1 and after culturing for 6 weeks.

FIG. 5. Trypan Blue cell viability assay for Donors C, D, E, F, and G (also referred to as donors 1, 2, 3, 4, and 5, respectively). Cell viability was determined for laser cut and hand cut cartilage particles. The average cell viability is presented as a percentage. The term "Denovo" refers to a juvenile cartilage product that is hand cut into 1 mm squares.

DETAILED DESCRIPTION OF THE INVENTION

I. Introduction

Figures 1A, 1B:
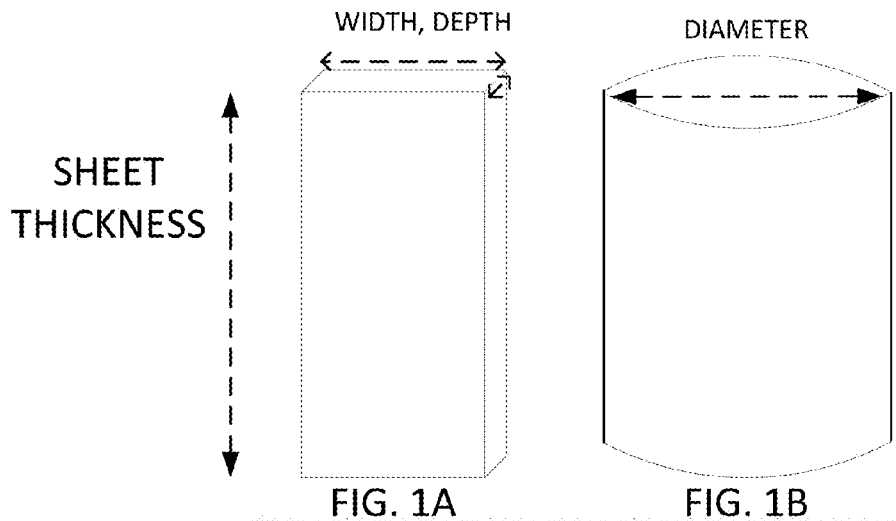
FIG. 1. Examples of cartilage particle shapes processed from cartilage tissue. (A) Cartilage particles can have a rectangular columnar shape. (B) Cartilage particles can have a cylindrical or elliptical columnar shape. (C) Cartilage particles can be cut into tiled or mosaic configurations. For example, the cartilage particle can have a width A, length B, and height C. Cuts, etches, or channels in the construct have a depth F and width H. Individual columns have a height F, width E, and length D. Subsequent to cutting, the construct has a minimum thickness G. (D) A cartilage tissue can be cut, for example using a laser, on two or more sides (e.g., top and bottom).

It is known in the art that juvenile cartilage contains more cells than adult cartilage. Furthermore, it has previously been suggested that the cells of adult cartilage do not grow out or have the ability to repair cartilage defects. Thus, it has been suggested that adult cartilage is not well suited for use in allogeneic grafts.

However, as described herein, it has been surprisingly discovered that adult cartilage, for example as prepared according to the methods described herein, retains properties that are useful in an allogeneic graft. As shown herein, it has been found that adult cartilage particles, when cultured for a period of time, exhibit comparable chondrocyte outgrowth and matrix production as juvenile cartilage particles. Thus, cartilage particles derived from human adult donors can be useful for repairing cartilage defects in subjects in need thereof.

II. Cartilage Compositions

In one aspect, cartilage compositions comprising viable chondrocytes are provided. In some embodiments, the composition comprises: a plurality of cartilage particles from a human adult cadaveric donor age 15 years or older, wherein the cartilage particles comprise viable chondrocytes; and a biocompatible carrier. In some embodiments, on average at least 50% of the chondrocytes in the cartilage particles are viable.

As used herein, the term "human adult donor" refers to a human donor that is fifteen years of age or older. The term "human juvenile donor" refers to a human donor that is twelve years of age or younger. In some embodiments, the donor is an adult cadaveric donor that is between the ages of 15 and 36 at the time of the donation. In some embodiments, the donor is an adult cadaveric donor that is 18 years of age or older at the time of the donation.

In some embodiments, the cartilage is articular cartilage. In some embodiments, the articular cartilage is obtained from an articular surface of a joint (e.g., a knee joint or an elbow joint) or from a long bone (e.g., femur or tibia).

Cartilage particles can be shaped as circles, spheres, squares, rectangles, cubes, cylinders, strips, tiles (e.g. particles that are partially attached to other particles), or other desired shapes. In some embodiments, the cartilage particles have an average thickness of about 0.25 mm to about 5 mm (e.g., about 0.25 mm, about 0.5 mm, about 0.75 mm, about 1 mm, about 1.5 mm, about 2 mm, about 2.5 mm, about 3 mm, about 3.5 mm, about 4 mm, about 4.5 mm, or about 5 mm). In some embodiments, the cartilage particles have an average thickness of about 0.5 mm to about 2 mm. In some embodiments, the cartilage particles have an average length and/or an average width of about 0.1 mm to about 25 mm (e.g., about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.5 mm, about 2 mm, about 2.5 mm, about 3 mm, about 3.5 mm, about 4 mm, about 4.5 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm). In some embodiments, the cartilage particles have an average length and/or an average width of about 0.5 mm to about 10 mm, of about 0.5 mm to about 5 mm, of about 0.5 mm to about 3 mm, of about 1 mm to about 5 mm, or of about 1 mm to about 3 mm.

In some embodiments, the cartilage particles have an average diameter of about 0.1 mm to about 25 mm (e.g., about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.5 mm, about 2 mm, about 2.5 mm, about 3 mm, about 3.5 mm, about 4 mm, about 4.5 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm). In some embodiments, the cartilage particles have an average diameter of about 0.5 mm to about 10 mm, of about 0.5 mm to about 5 mm, of about 0.5 mm to about 3 mm, of about 1 mm to about 5 mm, or of about 1 mm to about 3 mm.

In some embodiments, the cartilage particles have an average volume of from about 0.5 $mm^3$ to about 100 $mm^3$ (e.g., about 0.5 $mm^3$, about 1 $mm^3$, about 2 $mm^3$, about 3 $mm^3$, about 4 $mm^3$, about 5 $mm^3$, about 6 $mm^3$, about 7 $mm^3$, about 8 $mm^3$, about 9 $mm^3$, about 10 $mm^3$, about 15 $mm^3$, about 20 $mm^3$, about 25 $mm^3$, about 30 $mm^3$, about 35 $mm^3$, about 40 $mm^3$, about 45 $mm^3$, about 50 $mm^3$, about 60 $mm^3$, about 70 $mm^3$, about 80 $mm^3$, about 90 $mm^3$, or about 100 $mm^3$). In some embodiments, the cartilage particles have an average volume from about 0.5 $mm^3$ to about 30 $mm^3$. In some embodiments, the cartilage particles have an average volume from about 1 $mm^3$ to about 30 $mm^3$. In some embodiments, the cartilage particles have an average volume from about 1 $mm^3$ to about 25 $mm^3$.

As one non-limiting example, as shown in FIG. 1A, cartilage particles can have a rectangular columnar shape (e.g., with a thickness of 0.25 to 5 mm, a width of 1 to 5 mm, and a depth of 1-5 mm). As another non-limiting example, as shown in FIG. 1B, minced particles can have a cylindrical or elliptical columnar shape (e.g. with a thickness of 0.25 to 5 mm and a diameter of 1 to 5 mm).

Perforated Cartilage

In some embodiments, cartilage tissue can be cut into tiled or mosaic configurations to yield cartilage particles or constructs comprising channels or microperforations that separate the cartilage particles into a plurality of smaller portions. Thus, in some embodiments, the composition comprises one or more cartilage particles, each cartilage particle comprising one or more channels or microperforations that separates the cartilage particle into a plurality of smaller cartilage portions.

In some embodiments, the cartilage particle comprises one or more channels or microperforations that separates the cartilage particle into a plurality of smaller cartilage portions, wherein each cartilage portion has an average length and/or an average width of about 1 mm to about 5 mm (e.g., about 1 mm, about 1.5 mm, about 2 mm, about 2.5 mm, about 3 mm, about 3.5 mm, about 4 mm, about 4.5 mm, or about 5 mm). In some embodiments, the cartilage particle comprises one or more channels or microperforations that separates the cartilage particle into a plurality of smaller cartilage portions, wherein each cartilage portion has an average diameter of about 1 mm to about 5 mm (e.g., about 1 mm, about 1.5 mm, about 2 mm, about 2.5 mm, about 3 mm, about 3.5 mm, about 4 mm, about 4.5 mm, or about 5 mm).). In some embodiments, the cartilage particle comprises one or more channels or microperforations that separates the cartilage particle into a plurality of smaller cartilage portions, wherein each cartilage portion has an average volume of from about 0.5 $mm^3$ to about 100 $mm^3$ (e.g., about 0.5 $mm^3$, about 1 $mm^3$, about 2 $mm^3$, about 3 $mm^3$, about 4 $mm^3$, about 5 $mm^3$, about 6 $mm^3$, about 7 $mm^3$, about 8 $mm^3$, about 9 $mm^3$, about 10 $mm^3$, about 15 $mm^3$, about 20 $mm^3$, about 25 $mm^3$, about 30 $mm^3$, about 35 $mm^3$, about 40 $mm^3$, about 45 $mm^3$, about 50 $mm^3$, about 60 $mm^3$, about 70 $mm^3$, about 80 $mm^3$, about 90 $mm^3$, or about 100 $mm^3$).

Figure 1C:
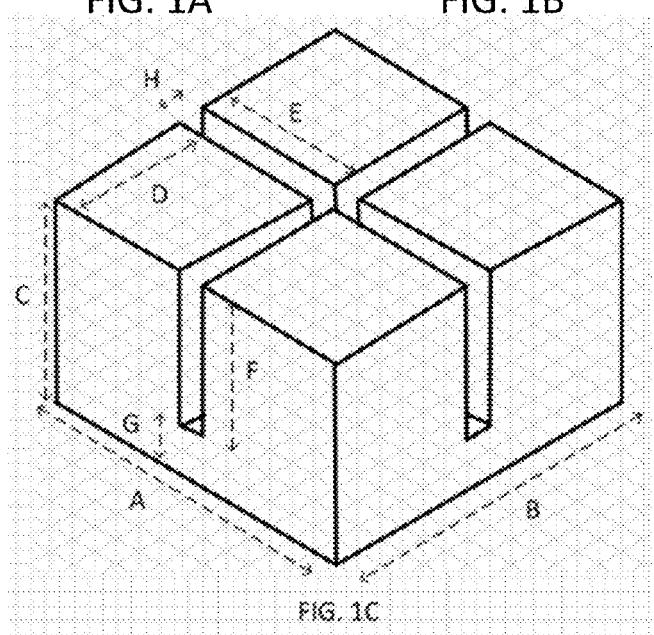
Figure 1D:
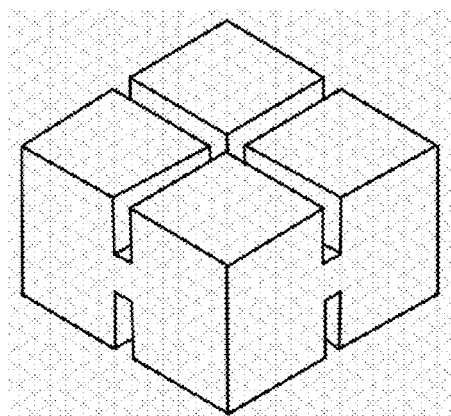

As a non-limiting example, in FIG. 1C, the cartilage construct or particle has a width A, length B, and height C. Cuts, etches, or channels in the construct have a depth F and width H. Individual columns have a height F, width E, and length D. Subsequent to cutting, the construct has a minimum thickness G. As shown in FIG. 1D, laser cutting can be performed on two or more sides of a cartilage tissue (e.g. top and bottom). Thus, it is possible to create cartilage constructs having multiple connected pieces of small columns or blocks, with square profiles, circular profiles, triangular profiles, irregular profiles, and the like. In some embodiments, cartilage constructs are prepared in strips, sheets, ribbons, zig-zag or accordion shapes, or the like. In some embodiments, the composition comprises one or more cartilage particles formed as a sheet, wherein the cartilage particle sheet comprises one or more channels or microperforations that separates the cartilage particle into a plurality of smaller cartilage portions.

Biocompatible Carrier

In some embodiments, the biocompatible carrier comprises a buffered solution. In some embodiments, the biocompatible carrier comprises a cryopreservation medium. In some embodiments, the cryopreservation medium comprises dimethyl sulfoxide (DMSO) and serum. In some embodiments, the biocompatible carrier comprises one or more cryoprotective agents such as, but not limited to, glycerol, DMSO, hydroxyethyl starch, polyethylene glycol, propanediol, ethylene glycol, butanediol, polyvinylpyrrolidone, or alginate.

In some embodiments, the biocompatible carrier comprises a growth medium. Suitable examples of growth medium include, but are not limited to, Dulbecco's Modified Eagle's Medium (DMEM) with 5% Fetal Bovine Serum (FBS). In some embodiments, growth medium includes a high glucose DMEM. In some embodiments, the biocompatible carrier (e.g., growth medium) comprises one or more antibiotics.

In some embodiments, the composition comprising the cartilage particles is formed into a paste.

Quantifying Viable Chondrocytes and Characterizing Cartilage Compositions

In some embodiments, the composition comprises cartilage particles having an average chondrocyte viability of at least 50%, at least 55%, at least 60%, at least 65%, at least 70%, at least 75%, at least 80%, at least 85% or higher. In some embodiments, the composition comprises cartilage particles having at least about 50,000, at least about 60,000, at least about 70,000, at least about 80,000, at least about 90,000, at least about 100,000, at least about 150,000, at least about 200,000, at least about 250,000, at least about 300,000, at least about 350,000, at least about 400,000, at least about 450,000, at least about 500,000, at least about 550,000, at least about 600,000, at least about 650,000, at least about 700,000, at least about 750,000, at least about 800,000, at least about 850,000, at least about 900,000, at least about 950,000, or at least about 1 million viable chondrocytes per cubic centimeter (cc). In some embodiments, the average chondrocyte viability or the amount of chondrocytes per cc is measured on day 1 following from the day of cutting.

The amount of chondrocytes in the cartilage particles can be measured by any of a number of cell counting assays. For example, in some embodiments, a Trypan Blue assay or a Presto Blue assay is used to quantify the number of chondrocytes in the cartilage particles. In some embodiments, the cartilage particles are cut from cartilage tissue on day 0 and then the amount of chondrocytes in the cartilage particles is measured on day 1. In some embodiments, the amount of chondrocytes and/or cell viability is measured on day 1, day 2, day 3, day 4, day 5, day 6, day 7, day 8, day 9, day 10, day 11, day 12, day 13, or day 14 from the day of cutting. In some embodiments, the amount of chondrocytes and/or cell viability is measured 1 week, 2 weeks, 3 weeks, 4 weeks, 5 weeks, or 6 weeks from the day of cutting. In some embodiments, for determining the amount of chondrocytes in a sample, the sample is subjected to digestion, e.g., with collagenase, in order to isolate chondrocytes for cell count and/or viability testing.

In some embodiments, a Trypan Blue assay is used to evaluate cell count and/or cell viability. The Trypan Blue assay is based upon the principle that viable cells do not take up impermeable dyes such as Trypan Blue, but dead cells are permeable and take up the dye. Typically, Trypan Blue stain is added to a sample, then the sample is mixed. An aliquot of the sample is placed on a cell counter slide and the number of cells is counted. The number of cells per cc is calculated based on the starting cartilage particle sample size.

In some embodiments, a Presto Blue assay is used to evaluate cell count and/or cell viability. The Presto Blue protocol involves an indirect chondrocyte cell count, using a metabolic assay. The cell count is performed by using a standard curve of known concentrations of chondrocytes to determine the count in the unknown samples. Typically, a 1:10 ratio of PrestoBlue® reagent (Life Technologies, Carlsbad, Calif.) to cell culture medium is added to a sample so that the sample is covered by the medium. The metabolic activity of the cells changes the color of the medium. After 3 hours incubation, 100 µA aliquots are taken from each sample and added to a multi-well plate for reading in a plate reader.

In some embodiments, a cell counting technique other than the Trypan Blue assay or Presto Blue assay is used to determine chondrocyte cell counts in a sample comprising cartilage particles. For example, the LIVE/DEAD® stain (Life Technologies, Carlsbad, Calif.) or the CellTiter-Glo® Luminescent Cell Viability Assay (Promega, Madison, Wis.) can be used to evaluate cell viability. In some embodiments, a Quant-iT™ DNA Assay Kit (Life Technologies, Carlsbad, Calif.), such as with PicoGreen, can be used to assess DNA content, thereby determining cell count.

In some embodiments, cell viability can be calculated using the following formula:

(number of live cells/total number of live+dead cells)*100%=viability percentage The cartilage particles can also be evaluated for characteristics of or chondrocyte outgrowth. For example, the cartilage particles can be cultured for a period of time (e.g., 1, 2, 3, 4, 5, or 6 weeks) and then assayed for one or more characteristics of chondrocyte outgrowth, such as glycosaminoglycan production, the presence of collagen, or the presence of one or more cartilage-specific biomarkers. In some embodiments, the cartilage particles exhibit one or more characteristics of chondrocyte outgrowth, including but not limited to glycosaminoglycan production, collagen content, or cartilage-specific biomarker expression, that is comparable to those obtained from cartilage particles from a juvenile donor and cultured under the same conditions.

In some embodiments, the cartilage particles exhibit glycosaminoglycan (GAG) production after being cultured for a period of time (e.g., as described herein in the Examples section). Chondrocytes function in part by producing GAGs and other components of the cartilaginous extracellular matrix. Hence, it is possible to evaluate the chondrocyte activity of cartilage tissue by observing glycosaminoglycan production. The glycosaminoglycan content can be measured, for example, using a dimethylmethylene blue (DMMB) assay or using Alcian Blue staining. In some embodiments, the levels of sulfated GAGs (sGAGs) are measured. sGAGS are an important component of healthy cartilage and can decrease with age and lead to the development of osteoarthritis. sGAGs can be measured, for example, using a commercially available sGAG Assay Kit (Kamiya Biomedical Company, Seattle, Wash.).

In some embodiments, the cartilage particles exhibit collagen production after being cultured for a period of time (e.g., as described herein in the Examples section). Collagen production and collagen content can be measured, for example, using a hydroxyproline assay (BioVison, Milpitas, Calif.). Collagen production and collagen content can also be measured using an immunoassay (e.g., immunohistochemistry or an immunosorbent assay, e.g, ELISA assay), including but not limited to a Collagen Type II Antibody Staining Protocol.

Additional Biological Components

In some embodiments, the cartilage particles are combined one or more other biological components in the composition. For example, in some embodiments, the cartilage particles are combined with a biological adhesive. Suitable biological adhesives include, but are not limited to, fibrin, fibrinogen, thrombin, fibrin glue (e.g., TISSEEL), polysaccharide gel, cyanoacrylate glue, gelatin-resorcin-formalin adhesive, collagen gel, synthetic acrylate-based adhesive, cellulose-based adhesive, basement membrane matrix (e.g., MATRIGEL®, BD Biosciences, San Jose, Calif.), laminin, elastin, proteoglycans, autologous glue, and combinations thereof.

In some embodiments, the cartilage particles are combined with demineralized bone matrix. For example, in some embodiments the cartilage particles are combined with demineralized bone matrix at a ratio of about 1 cubic centimeter (cc) demineralized bone matrix:4 cc cartilage particles to about 1 cc demineralized bone matrix:1 cc cartilage particles (e.g., about 4:1, about 3:1, about 2:1, or about 1:1 cc demineralized bone matrix:cartilage particles). Demineralized bone matrix can be prepared, e.g., by subjecting a bone substrate to acid, e.g., hydrochloric acid (HCl). Demineralized bone matrix is also commercially available.

In some embodiments, the cartilage particles are combined with cells such as stem cells. In some embodiments, the cartilage particles are combined with a bone or cartilage substrate that is seeded with stem cells. For example, in some embodiments, the cartilage particles are combined with a bone or cartilage substrate (e.g., cortical and/or cancellous bone substrate, demineralized cortical and/or cancellous bone substrate, an osteochondral substrate, or a cartilage substrate) that is seeded with mesenchymal stem cells. Stem cell-seeded bone and cartilage substrates and methods of preparing such substrates are described in U.S. 2010/0124776 and U.S. application Ser. No. 12/965,335, the contents of each of which are incorporated by reference herein.

III. Methods of Manufacturing Cartilage Compositions

In another aspect, methods of manufacturing cartilage compositions are provided. In some embodiments, the method comprises:
  obtaining cartilage tissue from a human adult cadaveric donor;
  mincing the cartilage tissue into a plurality of cartilage particles, wherein the cartilage particles comprise viable chondrocytes; and
  suspending the plurality of cartilage particles in a biocompatible medium.

In some embodiments, on average at least 50% of the chondrocytes in the cartilage particles are viable. In some embodiments, an average at least 50%, at least 55%, at least 60%, at least 65%, at least 70%, at least 75%, at least 80%, at least 85% or more of the chondrocytes in the cartilage particles are viable. In some embodiments, the cartilage particles comprise at least about 50,000, at least about 60,000, at least about 70,000, at least about 80,000, at least about 90,000, at least about 100,000, at least about 150,000, at least about 200,000, at least about 250,000, at least about 300,000, at least about 350,000, at least about 400,000, at least about 450,000, at least about 500,000, at least about 550,000, at least about 600,000, at least about 650,000, at least about 700,000, at least about 750,000, at least about 800,000, at least about 850,000, at least about 900,000, at least about 950,000, or at least about 1 million viable chondrocytes per cubic centimeter (cc). In some embodiments, the average chondrocyte viability or the amount of chondrocytes per cc is measured on day 1 following from the day of cutting. The amount of chondrocytes and/or number of viable chondrocytes in a cartilage particle sample can be measured as described herein, for example as described in Section II above.

In some embodiments, the cartilage tissue is harvested from an adult cadaveric donor that is 18 years of age or older at the time of the donation. In some embodiments, the cartilage tissue is harvested from an adult cadaveric donor that is between the ages of 15 and 36 at the time of the donation. Tissue can be harvested from any cartilaginous region of the cadaveric donor. In some embodiments, cartilage is harvested from the knee joint of the donor or from a long bone. In some embodiments, articular cartilage is harvested from the donor. In some embodiments, the cartilage that is obtained from the donor is sliced to a thickness of about 0.25 mm to about 5 mm (e.g., about 0.25 mm, about 0.5 mm, about 0.75 mm, about 1 mm, about 1.5 mm, about 2 mm, about 2.5 mm, about 3 mm, about 3.5 mm, about 4 mm, about 4.5 mm, or about 5 mm, or from about 0.5 mm to about 2 mm) before the mincing step.

In some embodiments, the cartilage tissue is minced by hand. In some embodiments, the cartilage tissue is minced using a cutting mechanism. In some embodiments, the cutting mechanism is a laser cutting apparatus, a mechanical blade, a manual cutting apparatus, a manual pressing apparatus, or the like. In some embodiments, the cutting mechanism comprises a pneumatic press, such as an air press or an oil press, or a screw press.

In some embodiments, the cartilage tissue is minced using a laser cutting apparatus. For example, in some embodiments, the laser cutting apparatus is a laser engraver. Non-limiting examples of suitable engraving lasers include $CO_2$ engraving lasers, such as the Epilog Zing 30 Watt $CO_2$ engraving laser. In some embodiments, the mincing step comprises cutting the cartilage tissue with the laser cutting apparatus at a speed from about 10% to about 50% (e.g., about 10%, about 15%, about 20%, about 25%, about 30%, about 35%, about 40%, about 45%, or about 50%), a power from about 0% to about 45% (e.g., about 0%, about 1%, about 2%, about 5%, about 10%, about 15%, about 20%, about 25%, about 30%, about 35%, about 40%, or about 45%), and a frequency from about 10 Hz to about 2400 Hz (e.g., about 10 Hz, about 20 Hz, about 30 Hz, about 40 Hz, about 50 Hz, about 60 Hz, about 70 Hz, about 80 Hz, about 90 Hz, about 100 Hz, about 150 Hz, about 200 Hz, about 250 Hz, about 300 Hz, about 350 Hz, about 400 Hz, about 450 Hz, about 500 Hz, about 550 Hz, about 600 Hz, about 650 Hz, about 700 Hz, about 750 Hz, about 800 Hz, about 850 Hz, about 900 Hz, about 950 Hz, about 1000 Hz, about 1100 Hz, about 1200 Hz, about 1300 Hz, about 1400 Hz, about 1500 Hz, about 1600 Hz, about 1700 Hz, about 1800 Hz, about 1900 Hz, about 2000 Hz, about 2100 Hz, about 2200 Hz, about 2300 Hz, or about 2400 Hz). In some embodiments, the mincing step comprising cutting the cartilage tissue with the laser cutter at a speed from about 10% to about 50%, a power from about 0% to about 45%, and a frequency from about 10 Hz to about 2400 Hz. In some embodiments, the mincing step comprising cutting the cartilage tissue with the laser cutter at a speed from about 20% to about 35%, a power from about 2% to about 45%, and a frequency from about 400 Hz to about 2400 Hz. In some embodiments, the mincing step comprises cutting the cartilage tissue with the laser cutting apparatus at a speed from about 25% to about 35%, a power from about 20% to about 45%, and a frequency from about 1400 Hz to about 2400 Hz. Suitable speeds, powers, and frequencies for cutting the cartilage tissue are shown in Table 1.

According to some embodiments, small cartilage pieces can be created by laser cutting at a certain energy level without sacrificing cell viability. For example, as surprisingly demonstrated herein, cartilage tissue can be cut using a laser cutter to yield cartilage particles in which at least about at least 50%, at least 55%, at least 60%, at least 65%, at least 70%, at least 75%, at least 80%, at least 85% or more of the chondrocytes in the cartilage particles are viable. In some embodiments, a laser cutting mechanism is used to produce pieces of shaved cartilage. In some embodiments, a laser cutter is used to mince the cartilage tissue into particles having an average length and/or an average width of about 1 mm to about 5 mm (e.g., about 1 mm, about 1.5 mm, about 2 mm, about 2.5 mm, about 3 mm, about 3.5 mm, about 4 mm, about 4.5 mm, or about 5 mm, or from about 1 mm to about 3 mm). In some embodiments, a laser cutter is used to mince the cartilage tissue into particles having an average diameter of about 1 mm to about 5 mm (e.g., about 1 mm, about 1.5 mm, about 2 mm, about 2.5 mm, about 3 mm, about 3.5 mm, about 4 mm, about 4.5 mm, or about 5 mm, or from about 1 mm to about 3 mm). In some embodiments, a laser cutter is used to mince the cartilage tissue into particles having an average volume of about 0.5 $mm^3$ to about 100 $mm^3$ (e.g., about 0.5 $mm^3$, about 1 $mm^3$, about 2 $mm^3$, about 3 $mm^3$, about 4 $mm^3$, about 5 $mm^3$, about 6 $mm^3$, about 7 $mm^3$, about 8 $mm^3$, about 9 $mm^3$, about 10 $mm^3$, about 15 $mm^3$, about 20 $mm^3$, about 25 $mm^3$, about 30 $mm^3$, about 35 $mm^3$, about 40 $mm^3$, about 45 $mm^3$, about 50 $mm^3$, about 60 $mm^3$, about 70 $mm^3$, about 80 $mm^3$, about 90 $mm^3$, or about 100 $mm^3$, e.g., from about 0.5 $mm^3$ to about 30 $mm^3$, from about 1 $mm^3$ to about 30 $mm^3$, or from about 1 $mm^3$ to about 25 $mm^3$).

In some embodiments, the mincing step comprises cutting the cartilage tissue into circles, spheres, squares, rectangles, cubes, cylinders, strips, sheets, ribbons, zig-zag or accordion shapes, tiles (e.g. particles that are partially attached to other particles), or other desired shapes. In some embodiments, the mincing step comprises cutting the cartilage tissue (e.g., using a laser cutter) into tiled or mosaic configurations, for example as shown in FIG. 1D.

Forming Perforated Cartilage

In some embodiments, the cartilage tissue is incompletely cut so as to form channels or microperforations that separate the cartilage tissue into smaller cartilage portions. For example, laser or other or cutting disruption means can be used to create microperforations, channels, bores, apertures, and other passages from one side of a cartilage construct to another side, or through individual blocks or segments of a tiled cartilage construct. Thus, in some embodiments, the method comprises:

obtaining cartilage tissue from a human adult cadaveric donor;

processing the cartilage tissue to form a cartilage construct comprising one or more microperforations or channels that separates the cartilage construct into a plurality of smaller cartilage portions, wherein the cartilage construct comprises viable chondrocytes; and suspending the cartilage construct in a biocompatible medium.

In some embodiments, the processing step comprises perforating the cartilage tissue with a laser cutter to form the one or more microperforations or channels. In some embodiments, the processing step comprises cutting the cartilage tissue with the laser cutting apparatus at a speed from about 20% to about 30% (e.g., about 20%, about 25%, or about 30%), a power from about 0% to about 8% (e.g., about 0%, about 1%, about 2%, about 5%, about 6%, about 7%, or about 8%), and a frequency from about 10 Hz to about 750 Hz (e.g., about 10 Hz, about 20 Hz, about 30 Hz, about 40 Hz, about 50 Hz, about 60 Hz, about 70 Hz, about 80 Hz, about 90 Hz, about 100 Hz, about 150 Hz, about 200 Hz, about 250 Hz, about 300 Hz, about 350 Hz, about 400 Hz, about 450 Hz, about 500 Hz, about 550 Hz, about 600 Hz, about 650 Hz, about 700 Hz, or about 750 Hz). In some embodiments, the processing step comprises separating the cartilage construct into a plurality of smaller cartilage portions, wherein each cartilage portion has an average length and/or an average width of about 1 mm to about 5 mm (e.g., about 1 mm, about 1.5 mm, about 2 mm, about 2.5 mm, about 3 mm, about 3.5 mm, about 4 mm, about 4.5 mm, or about 5 mm). In some embodiments, the processing step comprises separating the cartilage construct into a plurality of smaller cartilage portions, wherein each cartilage portion has an average diameter of about 1 mm to about 5 mm (e.g., about 1 mm, about 1.5 mm, about 2 mm, about 2.5 mm, about 3 mm, about 3.5 mm, about 4 mm, about 4.5 mm, or about 5 mm).). In some embodiments, the processing step comprises separating the cartilage construct into a plurality of smaller cartilage portions, wherein each cartilage portion has an average volume of from about 0.5 $mm^3$ to about 100 $mm^3$ (e.g., about 0.5 $mm^3$, about 1 $mm^3$, about 2 $mm^3$, about 3 $mm^3$, about 4 $mm^3$, about 5 $mm^3$, about 6 $mm^3$, about 7 $mm^3$, about 8 $mm^3$, about 9 $mm^3$, about 10 $mm^3$, about 15 $mm^3$, about 20 $mm^3$, about 25 $mm^3$, about 30 $mm^3$, about 35 $mm^3$, about 40 $mm^3$, about 45 $mm^3$, about 50 $mm^3$, about 60 $mm^3$, about 70 $mm^3$, about 80 $mm^3$, about 90 $mm^3$, or about 100 $mm^3$).

In some embodiments, such microperforations or passages may be on the order of tens of microns in dimension, or less. In some embodiments, such microperforations or passages may be on the order of millimeters in dimension, or less.

Further Processing Steps

In some embodiments, following the mincing step, the cartilage particles or constructs can be subjected to one or more additional processing steps prior to suspending the cartilage particles in the biocompatible carrier. In some embodiments, the cartilage particles are washed with a saline solution. In some embodiments, the cartilage particles are treated with one or more enzymes that promote the release of chondrocyte cells from cartilage matrix. For example, collagenase can be applied to help release chondrocyte cells from the cartilage matrix of the tissue particles. In some embodiments, the cartilage particles are mixed with collagenase and/or pronase and incubated in a growth medium such as Dulbecco's Modified Eagle's Medium (DMEM) for a suitable length of time for releasing the chondrocytes.

In some embodiments, the cartilage particles are combined with demineralized bone matrix. For example, in some embodiments the cartilage particles are combined with demineralized bone matrix at a ratio of about 1 cc:4 cc demineralized bone matrix:cartilage particles to about 1 cc:1 cc demineralized bone matrix:cartilage particles (e.g., about 4:1, about 3:1, about 2:1, or about 1:1 cc demineralized bone matrix:cartilage particles). Demineralized bone matrix can be prepared, e.g., by subjecting a bone substrate to acid, e.g., hydrochloric acid (HCl). Demineralized bone matrix is also commercially available.

In some embodiments, the cartilage particles are combined with cells such as stem cells. In some embodiments, the cartilage particles are combined with a bone or cartilage substrate that is seeded with stem cells. For example, in some embodiments, the cartilage particles are combined with a bone or cartilage substrate (e.g., cortical and/or cancellous bone substrate, demineralized cortical and/or cancellous bone substrate, an osteochondral substrate, or a cartilage substrate) that is seeded with mesenchymal stem cells. Stem cell-seeded bone and cartilage substrates and methods of preparing such substrates are described in U.S. 2010/0124776 and U.S. application Ser. No. 12/965,335, the contents of each of which are incorporated by reference herein.

In some embodiments, the cartilage particles are combined with a biological adhesive. Suitable biological adhesives include, but are not limited to, fibrin, fibrinogen, thrombin, fibrin glue (e.g., TISSEEL), polysaccharide gel, cyanoacrylate glue, gelatin-resorcin-formalin adhesive, collagen gel, synthetic acrylate-based adhesive, cellulose-based adhesive, MATRIGEL® (BD Biosciences, San Jose, Calif.), laminin, elastin, proteoglycans, and combinations thereof.

In some embodiments, the cartilage particles are suspended in a biocompatible carrier. In some embodiments, the biocompatible carrier comprises a buffered solution (e.g., an aqueous buffered solution). In some embodiments, the biocompatible carrier comprises a cryopreservation medium. In some embodiments, the cryopreservation medium comprises dimethyl sulfoxide (DMSO) and serum. In some embodiments, the biocompatible carrier comprises one or more cryoprotective agents such as, but not limited to, glycerol, DMSO, hydroxyethyl starch, polyethylene glycol, propanediol, ethylene glycol, butanediol, or polyvinylpyrrolidone.

IV. Therapeutic Uses of Cartilage Compositions

The cartilage compositions described herein can be used to treat subjects in need thereof. Without being bound to a particular theory, it is believed that the methods of mincing cartilage described herein can facilitate the migration of cells out of the cartilage. When cartilage particles are administered to a subject, chondrocytes can migrate out of the minced pieces and carry out repair and regeneration functions. For example, the chondrocytes can reproduce and form new cartilage via chondrogenesis. In this way, minced cartilage which is applied to a site within a patient can be used to treat cartilage and/or bone defects. For example, chondrocytes from the minced cartilage pieces can reproduce and generate new cartilage in situ. The newly established chondrocyte population and cartilage tissue can fill defects, and integrate with existing native cartilage and/or subchondral bone at the treatment site.

In some embodiments, the cartilage compositions described herein are administered to a subject having a bone or cartilage defect. In some embodiments, the composition is administered to a defect in cartilage, bone, ligament, tendon, meniscus, joint, or muscle. In some embodiments, the subject has a degenerative defect or injury. In some embodiments, the subject has a traumatic defect or injury. In some embodiments, the subject has osteoarthritis. In some embodiments, the subject has a muscle defect.

In some embodiments, the cartilage compositions described herein are administered to a subject to repair cartilage or promote cartilage growth or regeneration in the subject. In some embodiments, the composition is administered to a joint (e.g., knee joint), to bone (e.g., femur or humerus), or to cartilage.

In some embodiments, the cartilage compositions described herein are administered to a subject having soft tissue defects, for the repair and regeneration thereof. In some embodiments, the composition is administered to a ligament, tendon, or muscle. In some embodiments, the soft tissue defect is a sprain, strain, contusion, or stress injury to a ligament, tendon, or muscle.

In some embodiments, a cartilage composition as described herein is administered locally to the subject. In some embodiments, the composition is surgically implanted in the subject. In some embodiments, the composition is administered in a minimally invasive procedure, e.g., arthroscopy.

V. Kits

In still another aspect, kits comprising a cartilage composition as described herein are provided. In some embodiments, the kit comprises a composition comprising a plurality of cartilage particles from a human adult cadaveric donor, wherein the cartilage particles comprise viable chondrocytes; and a biocompatible carrier. In some embodiments, the kit comprises a composition comprising cartilage particles having an average thickness from about 0.25 mm to about 5 mm; having an average length, width, or diameter from about 1 mm to about 5 mm; and/or having an average volume of from about 0.5 mm$^3$ to about 100 mm$^3$.

In some embodiments, the kits are used for treating a subject having a defect in cartilage, bone, ligament, tendon, meniscus, joint, or muscle. In some embodiments, the kits are used for treating a subject having a degenerative defect or injury cartilage, bone, ligament, tendon, meniscus, joint, or muscle; a subject having a traumatic defect or injury cartilage, bone, ligament, tendon, meniscus, joint, or muscle; or a subject having osteoarthritis.

In some embodiments, a kit comprises a cartilage composition as described herein packaged in a container for storage and/or shipment. In some embodiments, the kit further comprises instructions for administering the composition.

In some embodiments, a kit comprises a composition comprising cartilage particles as described herein, optionally along with biological adhesive components (e.g. fibrinogen and thrombin, for a fibrin glue). In some embodiments, cartilage particles and biological adhesive (e.g., fibrin glue) components are packaged separately, and a surgeon or user adds the fibrin glue to the surgery site prior to placement of the cartilage. In some embodiments, the biological adhesive (e.g., fibrin glue) is combined with the cartilage particles prior to administration at the treatment site.

In some instances, a kit comprises the packaged cartilage particles with bone and/or stem cell components. For example, in some embodiments, a kit comprises cartilage particles with demineralized bone matrix. In some embodiments, a kit comprises cartilage particles with cells (e.g., stem cells). In some embodiments, a kit comprises cartilage particles with a bone or cartilage substrate seeded with cells (e.g., adipose derived mesenchymal adult stem cells combined with a bone substrate, as described in U.S. 2010/0124776, or adipose derived mesenchymal adult stem cells combined with an osteochondral or cartilage substrate, as described in U.S. application Ser. No. 12/965,335).

VI. Examples

The following examples are offered to illustrate, but not to limit, the claimed invention.

Example 1: Laser Cutting to Generate Minced Cartilage

Laser cutting techniques can provide a cost effective approach for the preparation of minced cartilage particles, with a decreased opportunity for tissue contamination during the mincing process. As described below, minced cartilage particles, tiles, mosaics, and the like as prepared by laser processing techniques showed cell viability results that were comparable to the cell viability results observed when using manual cutting techniques. By using a laser to prepare minced particles, cost, contamination, and processing time can be reduced. Further, it is possible to provide increased amounts of donor tissue product.

Tissue cutting experiments were performed using an Epilog Zing 30 Watt CO2 engraving laser on juvenile or adult cartilage slices. Table 1 shows the results of the tissue cutting experiments at varying speeds, powers, and frequencies.

TABLE 1

Laser Settings

| Speed(%) | Power(%) | Frequency(Hz) | Result/outcome: |
|---|---|---|---|
| A. Low Range Settings Test: 2 mm square pattern cut, 1 mm thick samples used | | | |
| 30 | 10 | 1350 | Etches tissue, no burning, doesn't cut entirely through(mosaic) |
| 30 | 10 | 1000 | Etches tissue, no burning, doesn't cut entirely through(mosaic) |
| 30 | 10 | 750 | Etches tissue, no burning, doesn't cut entirely through(mosaic) |
| 30 | 8 | 750 | Some browning of tissue, perforations through tissue |
| 25 | 8 | 750 | Completely cut through tissue, some brown edges |
| 25 | 8 | 650 | Completely cut through tissue, some brown edges |
| 25 | 8 | 400 | Completely cut through tissue, no browning |
| 25 | 5 | 400 | Etched tissue, some browning, does not cut entirely through |
| 25 | 5 | 300 | Etched tissue, no browning, does not cut entirely through |
| 20 | 5 | 300 | Etched tissue, no browning, nearly complete full thickness cut |
| 20 | 2 | 300 | Etched tissue, no browning, does not cut entirely through |
| 20 | 0 | 300 | Etched tissue, no browning, etching not very deep |
| 20 | 2 | 200 | Etched tissue, no browning, nearly complete full thickness cut |
| 20 | 2 | 100 | Etched tissue, no browning, nearly complete full thickness cut |
| 20 | 2 | 50 | Etched tissue, no browning, nearly complete full thickness cut |
| 20 | 2 | 25 | Etched tissue, no browning, nearly complete full thickness cut with perforations through tissue |
| 20 | 2 | 10 | Perforations (full thickness) only through tissue no complete etched line |
| 20 | 1 | 10 | Perforations only, not a full thickness cut |
| 20 | 0 | 10 | Perforations only, not a full thickness cut |
| 10 | 0 | 10 | Laser very slow moving, tissue etched with perforations(full thickness), no solid line cut |
| B. High Range Settings Test: 2 mm square pattern cut, 1 mm thick samples used | | | |
| 30 | 30 | 2000 | Some browning of edges, complete cut full thickness cut |
| 35 | 30 | 2000 | Less browning than above settings, complete full thickness cut |
| 35 | 35 | 2000 | Some browning of edges, complete cut full thickness cut |
| 35 | 35 | 2200 | Some browning of edges, complete cut full thickness cut |
| 35 | 40 | 2200 | Some browning of edges, complete cut full thickness cut |
| 35 | 40 | 2400 | Browning of edges, complete full thickness cut |
| 35 | 45 | 2400 | dark brown edges, complete cut through |

Based at least in part upon these findings, it was determined that laser settings at 25-35% speed, 2-45% power, and 400-2400 Hz frequency provide desirable results for mincing cartilage.

Example 2: Characterization of Minced Articular Cartilage from Adult or Juvenile Donors Fresh cadaveric adult and juvenile articular cartilage tissue samples were processed using either a laser cutting protocol or a hand cutting protocol. The adult donors were between fifteen and thirty six years of age, and the juvenile donors were between the ages of three months and 12 years. For the laser cutting method, the cartilage was shaved into thin slices (e.g., sheets having a thickness of 1-5 mm) using a scalpel, and the sliced sheets were minced into small particles (e.g., 1 mm, 2 mm, and/or 3 mm particles) using an Epilog Zing 30 Watt engraving laser. The laser cutting pattern was designed with a CorelDRAW® graphics software program. The cartilage was minced into square shaped particles, using energy levels and other laser parameters as described in Table 1. During the laser cutting procedure, the cartilage was maintained in a hydrated state. The minced particles were then washed with a phosphate buffered saline (PBS) solution.

Cartilage particles were characterized for cell count, cell viability, and chondrocyte growth as described below.

Figure 2:
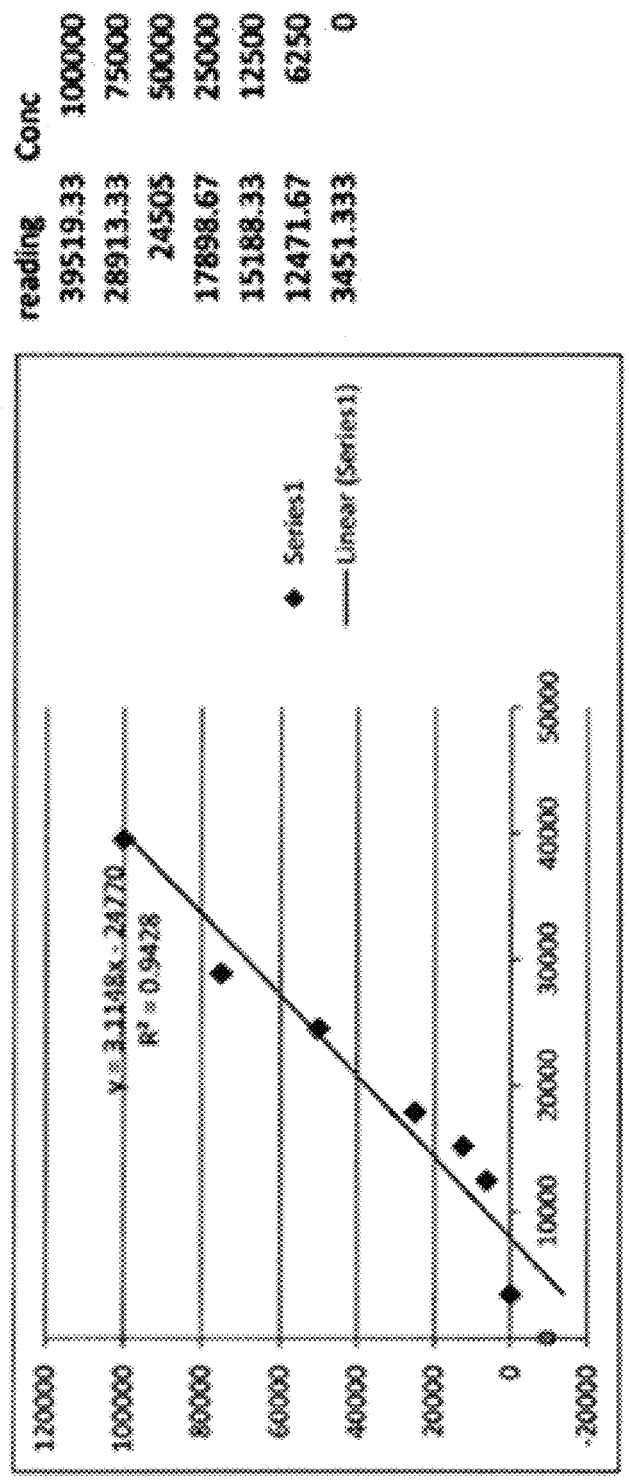
FIG. 2. A standard curve for samples having known concentrations of chondrocytes. The y-axis represents fluorescence readings from a Countess® automated cell counter, and the x-axis represents the chondrocyte concentration (cells/μl).

Using samples having known concentrations of chondrocytes, a standard curve was prepared as shown in FIG. 2. The y-axis represents fluorescence readings from a Countess® automated cell counter, and the x-axis represents the chondrocyte concentration (cells/µl).

Cell Counting, Donors A (Adult) and B (Juvenile), Day One:

Some of the harvested chondrocytes were tested for cell count on the day of mincing (day 1) using a Trypan blue staining protocol followed by analysis in a Countess® automated cell counter. Cartilage particles were digested with collagenase to isolate chondrocytes, and that mixture was then filtered through a 105 micron filter to separate any undigested matrix from the isolated cells. For the experiments illustrated by FIGS. 3A and 3B, equal amounts of chondrocyte samples were placed in the individual plate wells for evaluation.

Figure 3A:
FIG. 3. Mean fluorescence readings for (A) chondrocyte samples from adult donor A and (B) chondrocyte samples from juvenile donor B placed in six-well tissue culture plates.
Figure 3B:

As depicted in FIG. 3A, adult donor cartilage tissue that was minced with laser cutting provided a mean fluorescence reading of 21,636 (Std. Dev. 578; CV % 2.67), which corresponds to a cell count of 42,622 chondrocytes/µl, using the standard curve of FIG. 2. The adult donor cartilage tissue that was minced with hand cutting provided a mean fluorescence reading of 24,853 (Std. Dev. 1507; CV % 6.06), which corresponds to a cell count of 52,642 chondrocytes/µl. As depicted in FIG. 3B, juvenile donor cartilage tissue that was minced with laser cutting provided a mean fluorescence reading of 27,528 (Std. Dev. 2494; CV % 9.06), which corresponds to a cell count of 60,974 chondrocytes/µl. The juvenile donor cartilage tissue that was minced with hand cutting provided a mean fluorescence reading of 41,088 (Std. Dev. 3472; CV % 8.45), which corresponds to a cell count of 103,211 chondrocytes/µl. Based on these results, it was observed that in terms of cell count, there may be no large differences between the laser cutting and hand cutting methods.

FIG. 4 shows mean fluorescence readings as described above. The numbers were calculated using a standard curve and the fluorescence reading from a Presto Blue metabolic assay when evaluated in the plate reader. Six week cell counts were also performed using a Presto Blue assay.

Cell Counting, Donors C to G (Six Week):

To compare how chondrocytes from both adult and juvenile cartilage grow out of the cartilage matrix, a 6-week explant study was conducted. Three research-consented adult donors (donors C, E, and G) and two research-consented juvenile donors (donors D and F) were obtained. Samples were cut into sheets approximately 1 mm thick and minced by hand or laser cut into 2 mm cubes and measured into 0.3 ml aliquots. Cartilage particles were placed into plate wells along with TISSEEL fibrin glue (Baxter, Deerfield, Ill.), which provided a support from which the chondrocytes could grow out of the cartilage samples. No collagenase was used on the cells. Chondrocyte media (Cell Applications, San Diego, Calif.) was then added and changed twice weekly.

Cell counting was conducted after six weeks using either (A) a Trypan Blue staining protocol followed by analysis in a Countess® automated cell counter, or (B) a Presto Blue staining protocol followed by analysis in a Synergy™ H1 hybrid plate reader. The Presto Blue protocol involves an indirect chondrocyte cell count, using a metabolic assay. The cell count is performed by using a standard curve of known concentrations of chondrocytes to determine the count in the unknown samples. Typically, where the chondrocytes are combined with fibrin, a metabolic assay and hybrid reader can be used to indirectly determine the chondrocyte cell count, by evaluating the metabolic activity. Here, it may be assumed that a majority of the cells (e.g., 95% to 98% or more) are viable.

FIG. 5 shows the live cell number count and viability results for the Trypan Blue protocol, and the live cell count number results for the Presto Blue protocol. As depicted in the Trypan Blue live cell test results, there were 1,052,167±989,536 of live cells per cc of fresh cartilage using laser cutting, and 375,333±295,846 live cells per cc of fresh cartilage using hand cutting.

Figure 6:
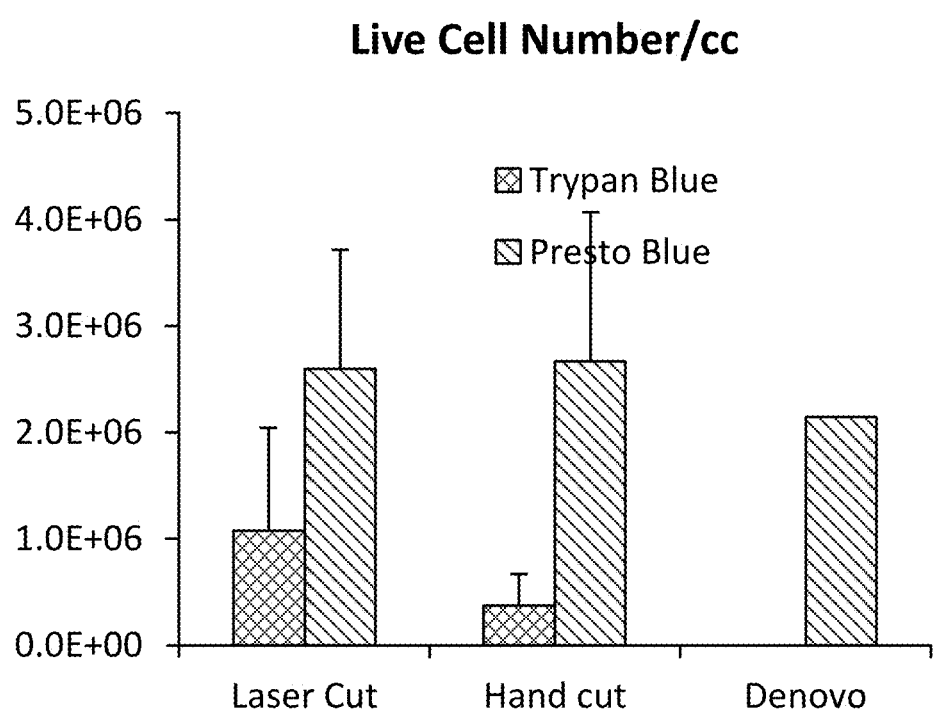
FIG. 6. Graph depicting the live cell count data for Trypan Blue and Presto Blue assays shown in the lower panel of FIG. 5.

FIG. 6 shows the live cell count number results for the Trypan Blue and Presto Blue protocols, and is based on cell count data shown in FIG. 5. With regard to the Trypan Blue and Presto Blue cell count results shown here, a single ANOVA analysis was performed and there was no significant difference using these two methods regarding live cell number.

Figure 7:
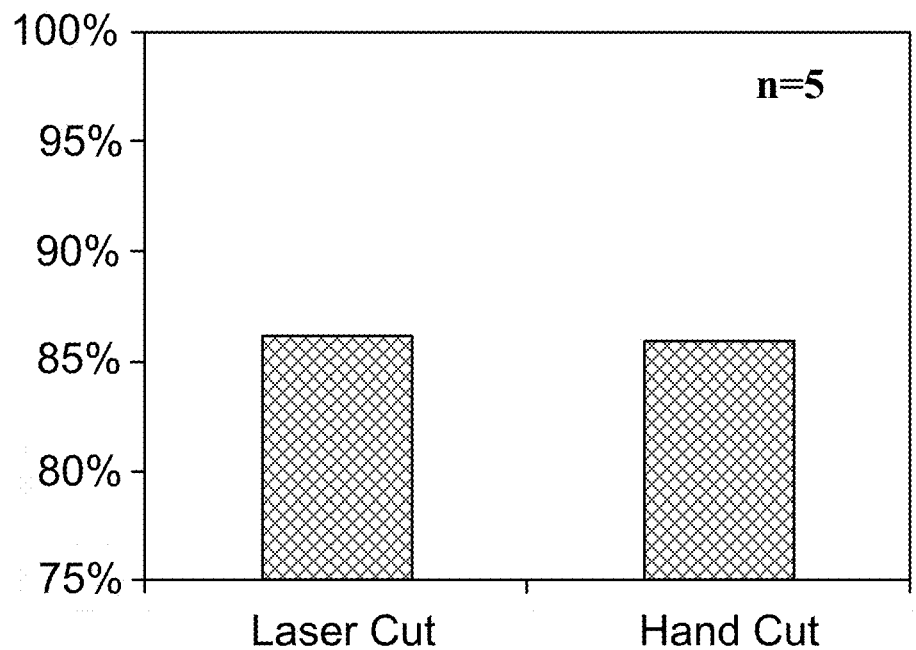
FIG. 7. Trypan Blue cell viability assay at 6 weeks for laser cut and hand cut cartilage particles.

Cell Counting, Donors C to G:

FIG. 7 shows day 1 (i.e., one day after cutting) cell viability assay for Donors C to G using the Trypan Blue protocol, which are based on the viability % results depicted in FIG. 5. As depicted here, the average cell viability is about 86% for both laser cut cartilage and hand cut cartilage. Hence, it was observed that cartilage tissue can be minced with laser cutting, without sacrificing cell viability relative to hand cutting methods. With regard to the Trypan Blue viability results shown in FIG. 7, a single ANOVA analysis was performed and there was no significant difference using these two methods regarding cell viability.

Figures 8A, 8B:
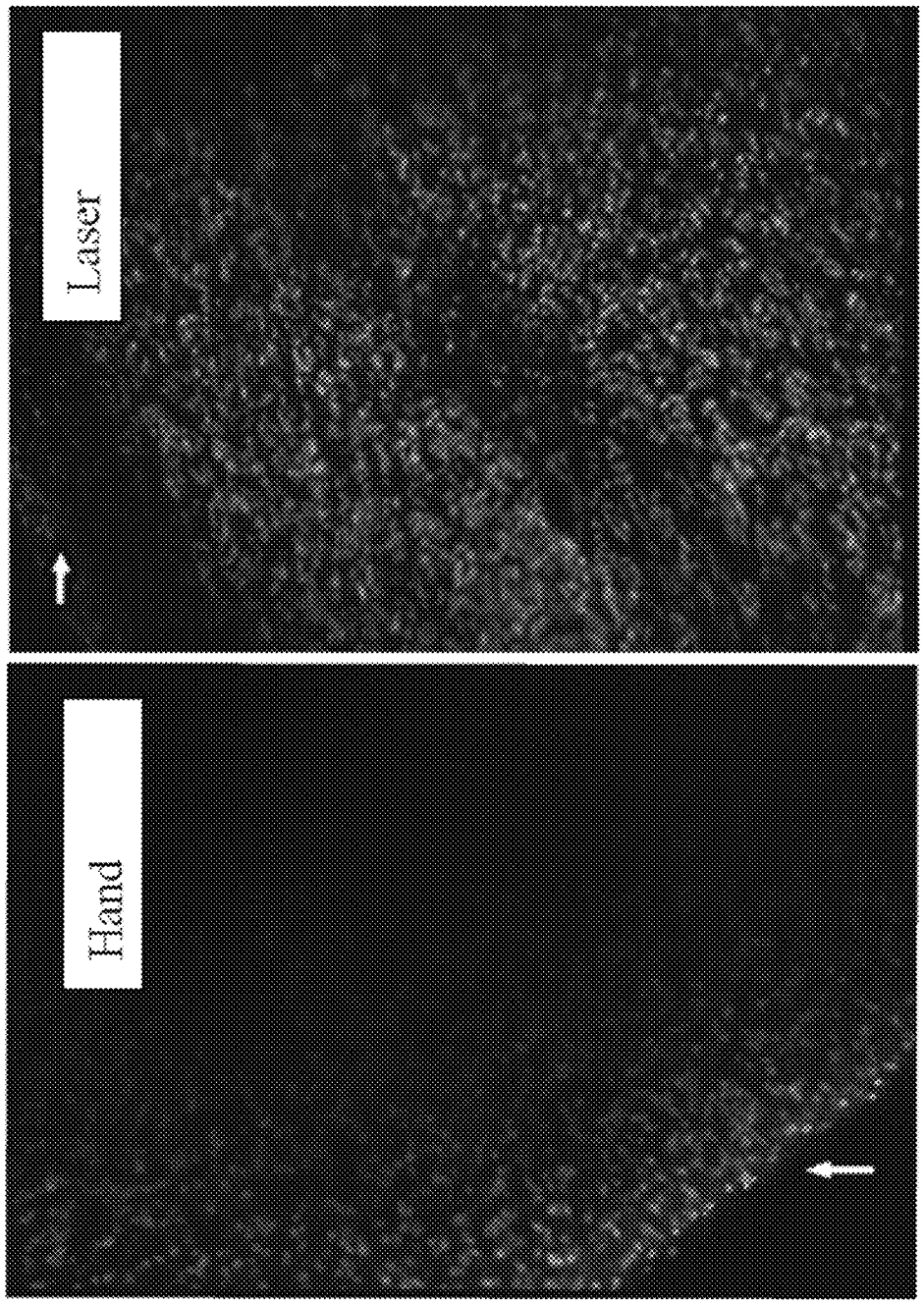
FIG. 8. Confocal microscope images depicting tissue edges (white arrow) of hand cut (A) and laser cut (B) cartilage pieces. Invitrogen LIVE/DEAD® stain was used on undigested cartilage sample for visualizing cells.

FIGS. 8A and 8B are confocal microscope images depicting tissue edges (white arrow) of hand cut and laser cut (respectively) cartilage pieces. These results indicate that there was not a significant difference of cell viability when comparing laser cut and hand cut cartilage tissue samples. For this study, LIVE/DEAD® stain (Life Technologies, Carlsbad, Calif.) was used. Briefly, undigested cartilage particles were placed in wells of a 24-well plate. 1 ml PBS was added to each well and 0.5 µl of the red and green dye was then added. The plates were covered with foil and allowed to sit for a minimum of 15 minutes. The cartilage particles were then placed on slides and the images captured by confocal microscopy on the laser setting.

It was also observed that laser cutting could be accomplished more quickly than hand cutting. For example, an equivalent amount of tissue could be minced in 8 hours via manual cutting, versus 0.5 hours via laser cutting. Moreover, it was observed that it was easier to obtain uniformly shaped tissue pieces using laser cutting, as compared with hand cutting.

Figure 9B:
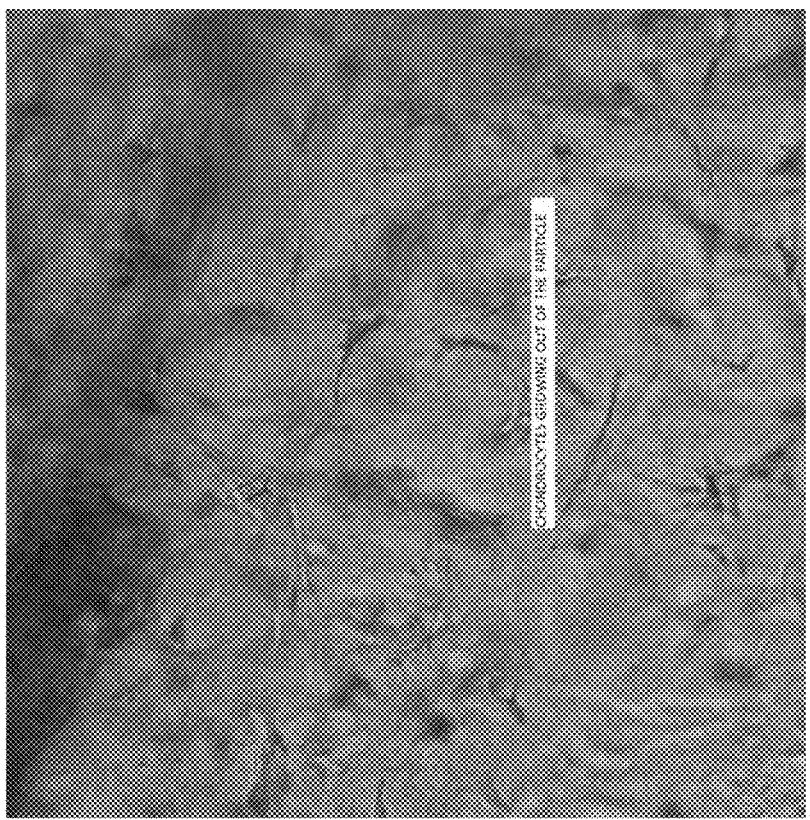
FIG. 9. Photographic images at 4× magnification of chondrocyte cells growing out of hand cut (A) and laser cut (B) adult cartilage particles. Cartilage particles were placed in 12-well culture plates with chondrocyte growth medium containing 10% FBS and 2% antibiotic. The medium was changed twice a week. The plates were cultured under standard cell culture conditions (37° C. incubator with 5% $CO_2$) and the images were obtained at 18 days.
Figure 9A:
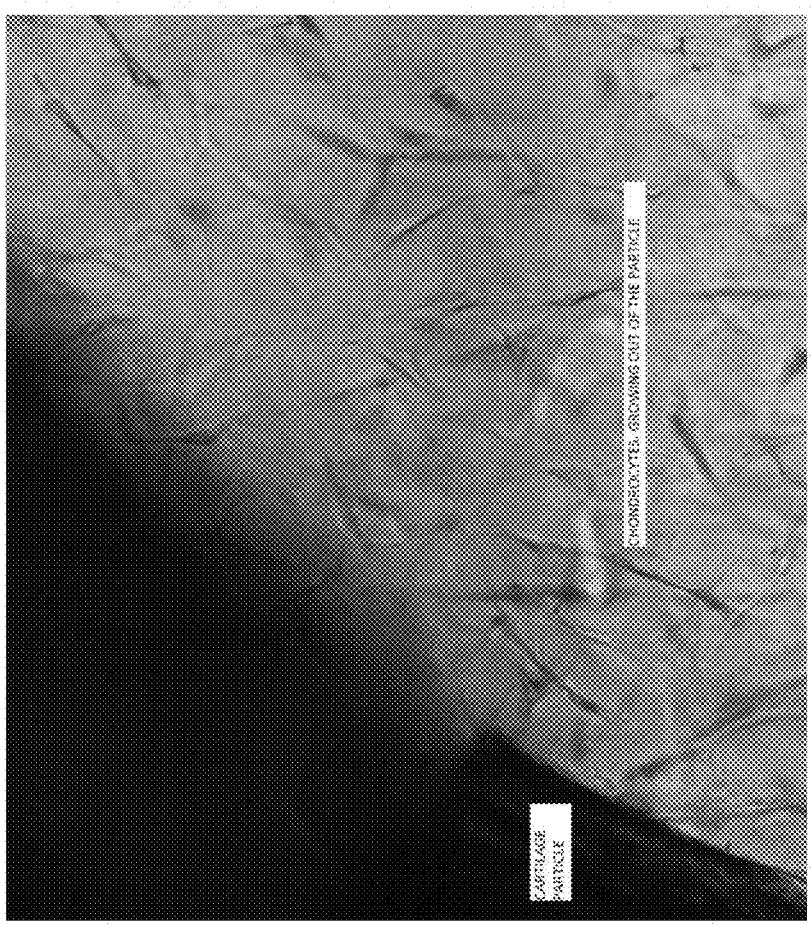
Figure 10:
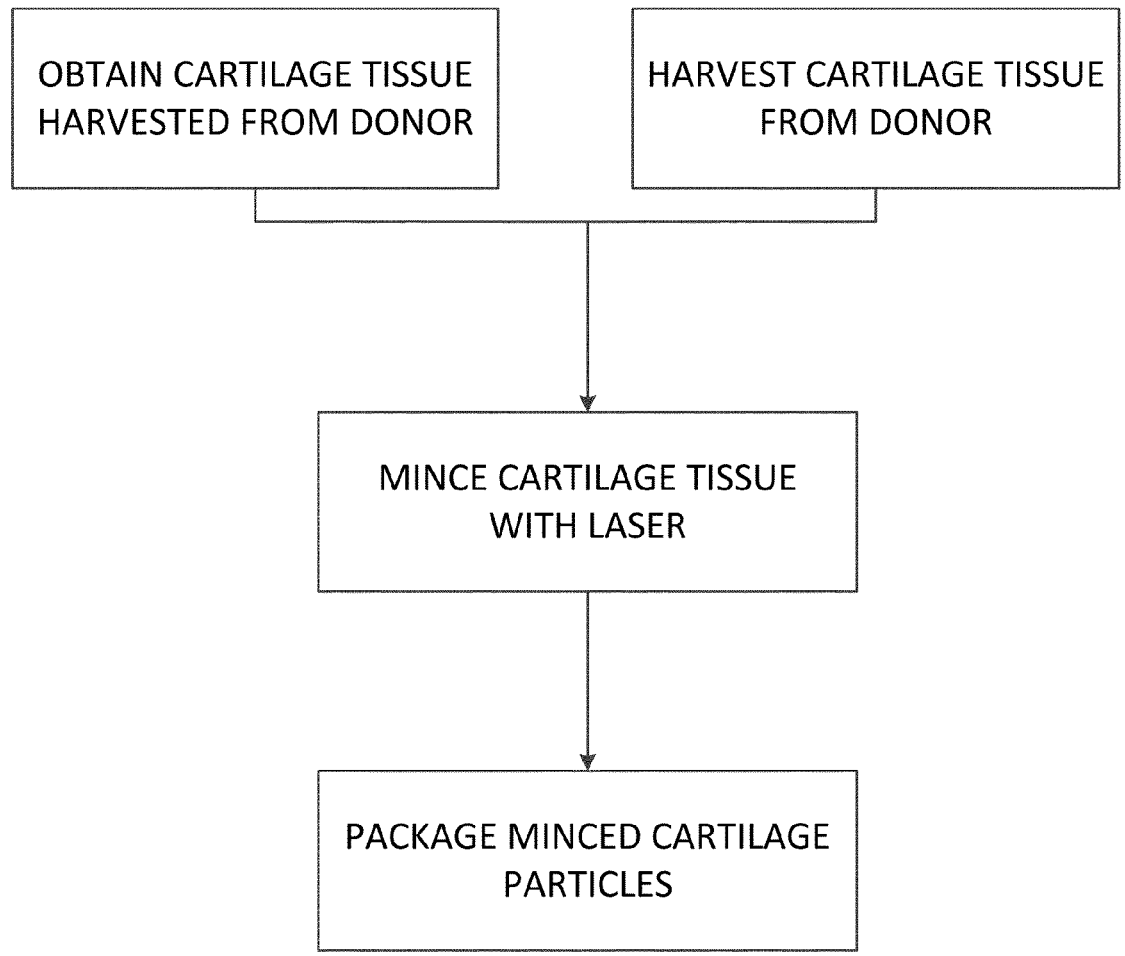
FIG. 10. Schematic of an exemplary manufacturing method for cartilage compositions.

Microscopy Observations at Eighteen Days:

FIGS. 9A and 9B provide photographic images of chondrocyte cells growing out of hand cut (FIG. 9A) and laser cut (FIG. 9B) adult cartilage particles. Specifically, cartilage was obtained from an adult donor, and minced with either laser cutting or manual cutting protocols. The minced cartilage particles were placed in 12 well culture plates, using chondrocyte growth medium with 10% FBS and 2% antibiotic. The media was changed twice a week. The plates were cultured in a 37° C. incubator with 5% $CO_2$ (e.g. standard cell culture conditions). The images (4× magnification) were obtained at 18 days. As shown here, chondrocytes were observed to grow out of the minced particles.

Figure 11:
FIG. 11. Alcian Blue staining of cartilage samples from adult (upper panels) and juvenile (lower panels) donors after a 6 week explant study.
Figure 11:
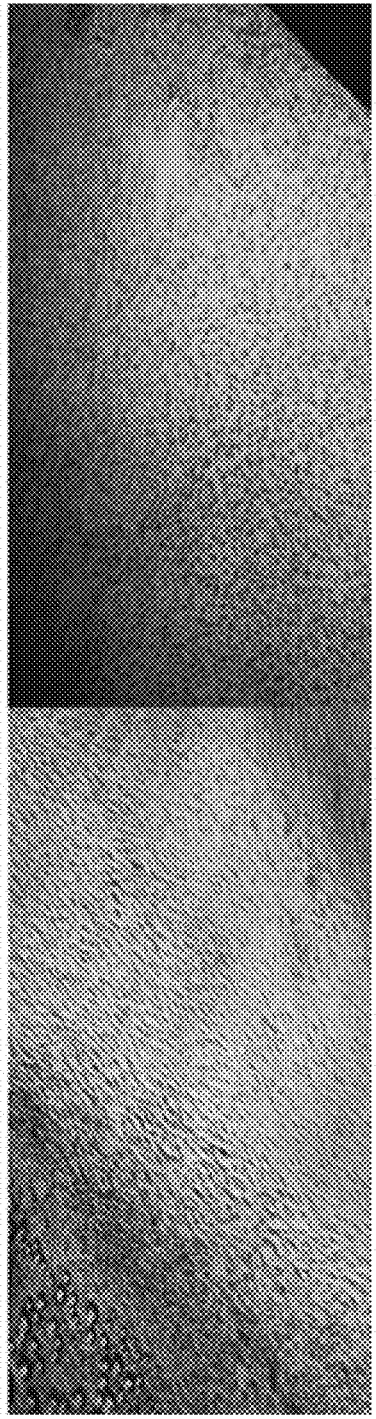

Alcian Blue Staining at Six Weeks:

After six week of culture, samples were fixed and stained using Alcian Blue (IHC world, Woodstock, Md.) to show glycosaminoglycan content. As shown in FIG. 11, both adult laser cut cartilage particles and juvenile laser cut cartilage particles stained positive for the presence of glycosaminoglycans after 6 weeks.

Example 3: 12-Week Explant Study to Characterize Cartilage Samples

To further compare chondrocyte outgrowth and matrix production between adult and juvenile donors, a 12-week explant study was performed. Three research consented adult donors and two research consented juvenile donors were obtained. Samples were sliced by hand into 1 mm thick sheets and laser cut into 2 mm cubes. The samples were measured into 0.3 ml aliquots (5 samples per donor) and glued to a 12 well plate using TISSEEL (Baxter, Deerfield, Ill.) for a 12 week explant study to be performed. A 1:10 ratio of PrestoBlue® (Life Technologies, Carlsbad, Calif.) to media was used for weekly cell counting. Collagen type II immunohistochemistry was performed on samples after the 12 week time point, as well as sulfated glycosaminoglycans (sGAG) assay (Kamiya Biomedical Company, Seattle, Wash.), hydroxyproline assay (BioVison, Milpitas, Calif.), and DNA analysis with a Pico Green Assay (Invitrogen, Grand Island, N.Y.). All outcome measures were evaluated using single ANOVA analysis. Significance was considered as $p \leq 0.05$.

Results:

The 12-week study confirmed a similar trend of cell outgrowth and matrix production as was demonstrated in the 6-week explant study. The results of the hydroxyproline assay, Pico Green assay, and sGAG assay are presented in Table 2 below.

TABLE 2

| | Assay results | | | | | |
|---|---|---|---|---|---|---|
| | Result | | Standard Deviation | | P- | Statistically |
| Assay | Adult | Juvenile | Adult | Juvenile | value | Different? |
| Hydroxyproline (ug/well) | 17.1413 | 13.48556 | 0.215065 | 0.997325 | 0.9 | NO |
| DNA (ng/mL) | 3773.414 | 4168.478 | 677.499 | 365.6574 | 0.87 | NO |
| sGAG(ug/mL) | 268929 | 242163.9 | 9485.124 | 18392.75 | 0.985 | NO |

Figure 12:
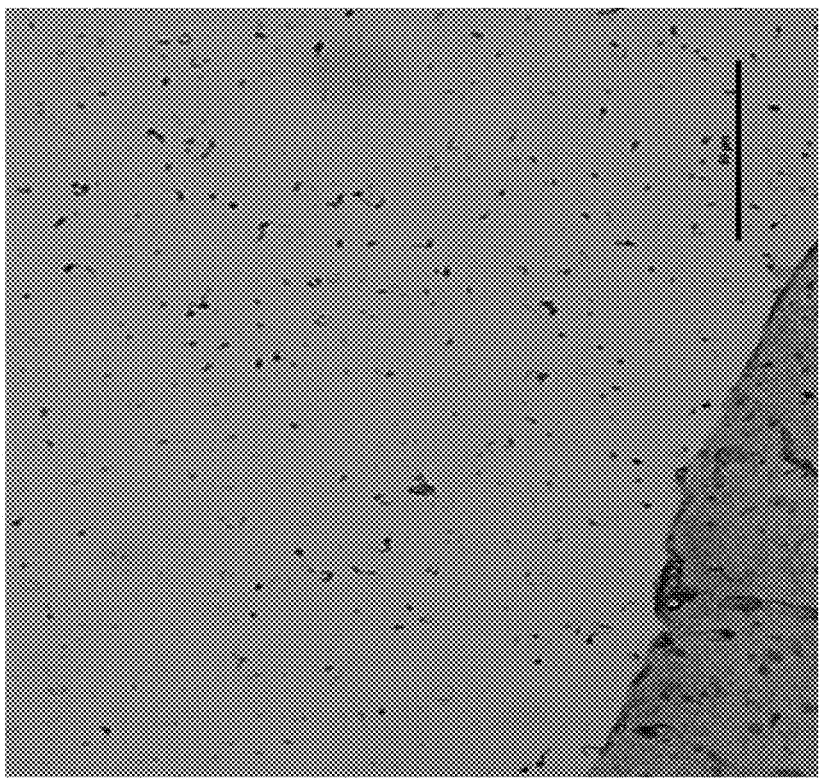
FIG. 12. Collagen type II staining of cartilage samples from adult cartilage (left panel) and juvenile cartilage (right panel) after a 12 week explant study. Brown staining in both the adult cartilage and juvenile cartilage indicates collagen type II produced by cells that grew out of the cartilage.
Figure 12:
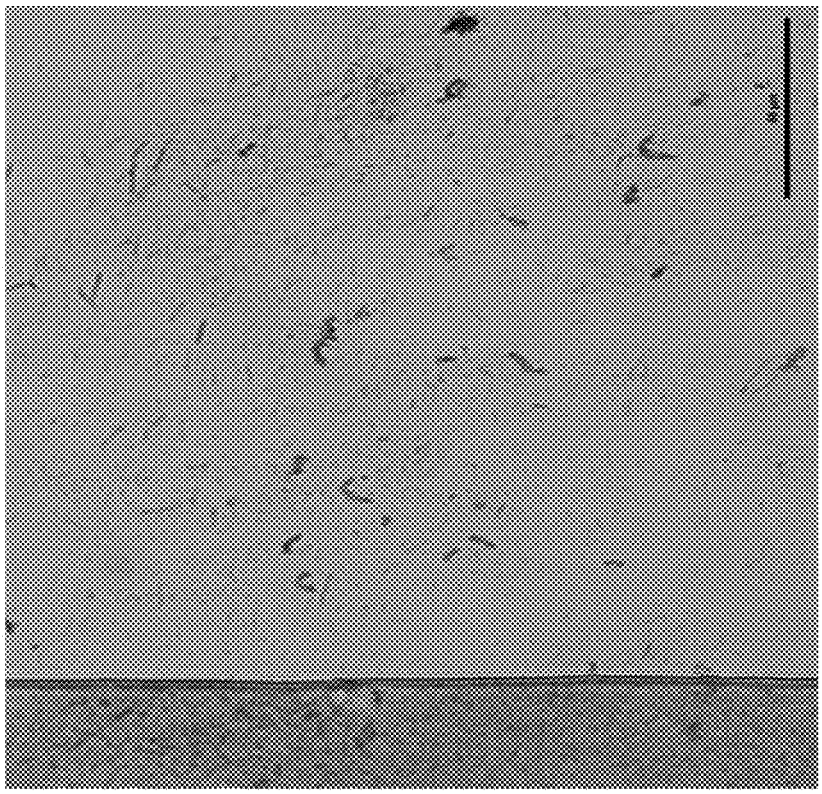

A hydroxyproline assay was used to determine the content of collagen in the explants; since about 13% of cartilage is hydroxyproline, the content was divided by 0.13 to obtain the collagen content. As shown in Table 2, adult donors had a total collagen content of 17.14±1.65 mg/ml. Juvenile donors had a total of 13.48±7.67 mg/ml, resulting in no statistical difference. sGAGS are an important component of healthy cartilage and can decrease with age and lead to the development of osteoarthritis. sGAG content for adult cartilage was 268929±9485 μg/mL, while sGAG content for juvenile donors was 242163.9±18392 μg/mL of sGAG, showing that sGAG content has no statistical difference. DNA content was calculated to estimate the total number of cells, based on the assumption that there are approximately 6 μg DNA per cell. After the 12-week explant study, adult donors had an average of 628902±112916 cells and juvenile donors had an average of 694746±60942 cells, showing that the total number of cells in adult and juvenile donors after 12 weeks of outgrowth was not statistically different. Collagen Type II IHC staining showed that both groups have type II collagen allowing for hyaline cartilage production (FIG. 12).

Although the foregoing invention has been described in some detail by way of illustration and example for purposes of clarity of understanding, one of skill in the art will appreciate that certain changes and modifications may be practiced within the scope of the appended claims. In addition, each reference provided herein in incorporated by reference in its entirety to the same extent as if each reference was individually incorporated by reference.

What is claimed is:

1. A method of manufacturing a cartilage composition, the method comprising:
   obtaining cartilage tissue from a human adult cadaveric donor age 15 years or older;
   mincing the cartilage tissue into a plurality of cartilage particles having an average volume from about 1 $mm^3$ to about 30 $mm^3$ using a laser cutter at a power of about 3 Watts to about 13.5 Watts and a frequency of about 400 Hz to about 2400 Hz, wherein the cartilage particles comprise chondrocytes native to the cartilage tissue, and wherein at least 50% of the chondrocytes present in the plurality of cartilage particles are viable;
   suspending the plurality of cartilage particles in a biocompatible carrier; and
   packaging the suspended plurality of cartilage particles into a container.

2. The method of claim 1, wherein the cartilage tissue is articular cartilage tissue.

3. The method of claim 1, wherein the cartilage tissue is from a human donor that is 18 years of age or older at the time of donation.

4. The method of claim 1, wherein prior to the mincing step, the cartilage tissue is sliced to a thickness of about 0.25 mm to about 5 mm.

5. The method of claim 1, wherein the mincing step comprises cutting the cartilage tissue with a laser cutter, with a mechanical blade, or with a mechanical press.

6. The method of claim 1, wherein the cartilage tissue is minced into a plurality of cartilage particles having an average width from about 1 mm to about 5 mm.

7. The method of claim 1, wherein the cartilage tissue is minced into a plurality of cartilage particles having an average diameter from about 1 mm to about 5 mm.

8. The method of claim 1, wherein following the mincing step, the plurality of cartilage particles are washed with a saline solution.

9. The method of claim 1, wherein the biocompatible carrier comprises a cryopreservation medium.

10. The method of claim 1, wherein prior to the suspending step, the method further comprises combining the plurality of cartilage particles with a biological adhesive.

11. The method of claim 1, wherein prior to the suspending step, the method further comprises combining the plurality of cartilage particles with demineralized bone.

12. The method of claim 1, wherein prior to the suspending step, the method further comprises combining the plurality of cartilage particles with a bone or cartilage substrate seeded with stem cells.

13. The method of claim 1, wherein the plurality of cartilage particles comprise at least 50,000 viable cells per $cm^3$.

14. The method of claim 1, wherein the biocompatible carrier comprises one or more cryoprotective agents, selected from the group consisting of glycerol, DMSO, hydroxyethyl starch, polyethylene glycol, propanediol, ethylene glycol, butanediol, polyvinylpyrrolidone, and alginate.

15. The method of claim 1, wherein the biocompatible carrier comprises a growth medium.

16. The method of claim 1, wherein the plurality of cartilage particles are in the shape of circles, spheres, squares, rectangles, cubes, cylinders, strips, sheets, ribbons, Zig-Zag shapes, or accordion shapes.

17. The method of claim 1, wherein prior to the suspending step, the method further comprises treating the plurality of cartilage particles with one or more enzymes that promote the release of chondrocyte cells from cartilage particles.

18. The method of claim 17, wherein the one or enzymes comprise at least one of collagenase or pronase.

* * * * *